US00PP32061P2

(12) United States Plant Patent
Arts

(10) Patent No.: US PP32,061 P2
(45) Date of Patent: Aug. 11, 2020

(54) ***DIANTHUS* PLANT NAMED 'DDTSS12-0'**

(50) Latin Name: ***Dianthus* hybrid**
Varietal Denomination: DDTSS12-0

(71) Applicant: Niels Arts, Aalsmeer (NL)

(72) Inventor: Niels Arts, Aalsmeer (NL)

( * ) Notice: Subject to any disclaimer, the term of this patent is extended or adjusted under 35 U.S.C. 154(b) by 0 days.

(21) Appl. No.: 16/602,502

(22) Filed: Oct. 17, 2019

(51) Int. Cl.
*A01H 5/02* (2018.01)
*A01H 6/30* (2018.01)

(52) U.S. Cl.
USPC ..... Plt./273

(58) Field of Classification Search
USPC ..... Plt./272, 273
See application file for complete search history.

*Primary Examiner* — Susan McCormick Ewoldt
(74) *Attorney, Agent, or Firm* — Cassandra Bright

(57) ABSTRACT

A new and distinct *Dianthus* cultivar named 'DDTSS12-0' is disclosed, characterized by unique bi-color double flowers. Plants bloom for an extended period into the Summer and are hardy to USDA Zone 5. The new variety is a *Dianthus*, typically produced as a garden or container plant.

2 Drawing Sheets

Figure 1:
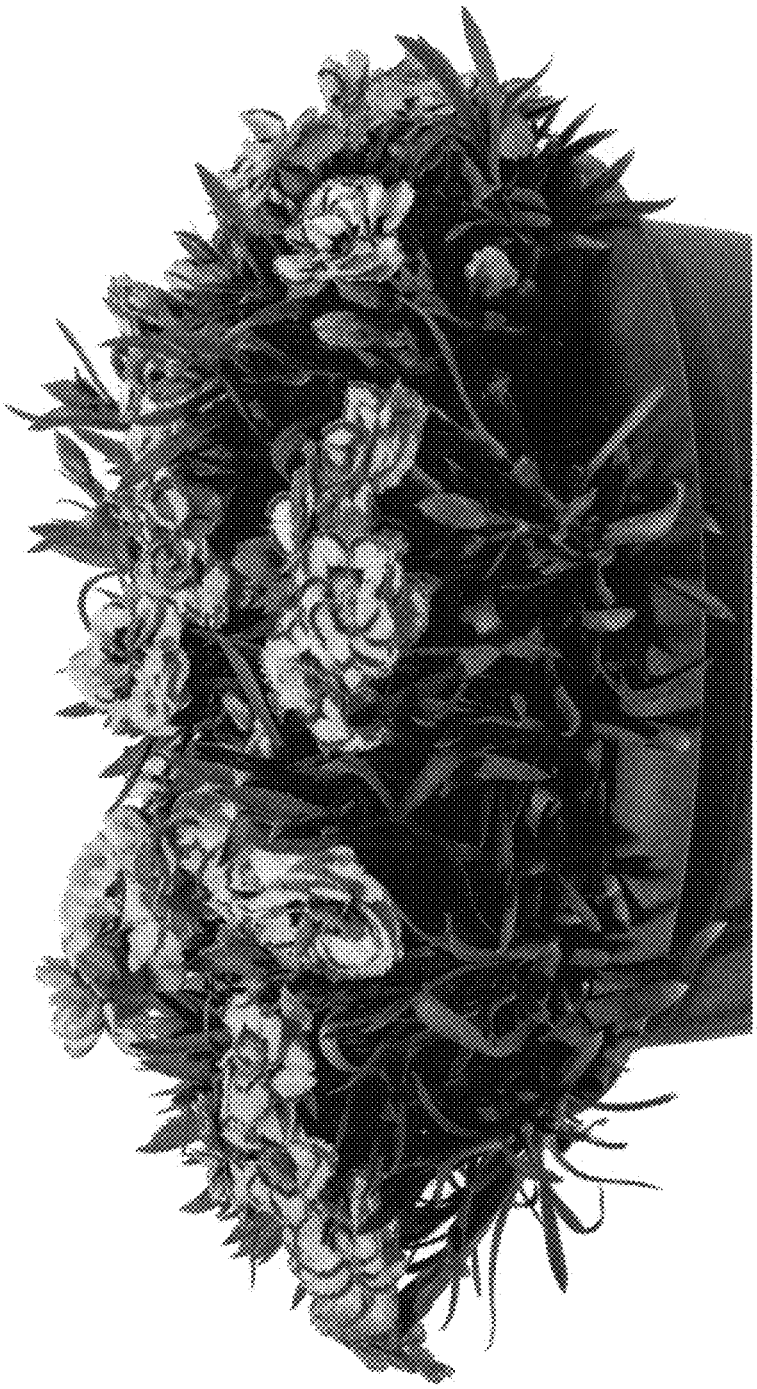

Latin name of the genus and species: *Dianthus* hybrid.
Variety denomination: 'DDTSS12-0'.

BACKGROUND OF THE INVENTION

The new cultivar is a product of a planned breeding program. The new variety originated as the result of the crossing of the female parent, an unpatented, proprietary *Dianthus* referred to as '13-0309-003' and the pollen parent, a different unpatented proprietary *Dianthus* referred to as '14-0205-003'. 'DDTSS12-0' was discovered and selected by the inventor, Niels Arts at a commercial greenhouse in Santa Paula, Calif., in May of 2017.

Asexual reproduction of the new cultivar 'DDTSS12-0' was first performed in Santa Paula, Calif. at a research greenhouse by vegetative terminal cuttings in April of 2018. 'DDTSS12-0' has since produced several generations and has shown that the unique features of this cultivar are stable and reproduced true to type.

SUMMARY OF THE INVENTION

The cultivar 'DDTSS12-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DDTSS12-0'. These characteristics in combination distinguish 'DDTSS12-0' as a new and distinct *Dianthus* cultivar:

1. Unique bi-color pink and red flowers.
2. Day-length neutral flowering.
3. Suitability for both garden and container uses.
4. Extended bloom time into Summer months.
5. Hardy to USDA Zone 5.

PARENTAL COMPARISON

Plants of the new cultivar 'DDTSS12-0' are comparable to the seed parent in most horticultural characteristics; however, the new variety 'DDTSS12-0' differs in the following:

1. The new variety produces lighter pink bicolor flowers than the seed parent.
2. Foliage of the new variety is brighter green than foliage of this comparator.

Plants of the new cultivar 'DDTSS12-0' are comparable to the pollen parent in most horticultural characteristics; however, the new variety 'DDTSS12-0' differs in the following:

1. The new variety produces double flowers, the pollen parent produces single flowers.

COMMERCIAL COMPARISON

Plants of the new cultivar 'DDTSS12-0' are comparable to the commercial *Dianthus* variety 'DDTHP02-0', U.S. Plant Pat. No. 28,102. The two *Dianthus* varieties are similar in most horticultural characteristics; however, the new variety 'DDTSS12-0' differs in the following:

1. The new variety produces bicolor flowers while this comparator has solid pink flowers.
2. Foliage of the new variety is brighter green than foliage of this comparator.

Plants of the new cultivar 'DDTSS12-0' are comparable to the commercial *Dianthus* variety 'DCACR08-0', U.S. Plant Pat. No. 30,026. The two *Dianthus* varieties are similar in most horticultural characteristics; however, the new variety 'DDTSS12-0' differs in the following:

1. The new variety produces bicolor flowers while this comparator has solid dark pink flowers.
2. Foliage of the new variety is brighter green than foliage of this comparator.

BRIEF DESCRIPTION OF THE PHOTOGRAPHS

The accompanying photograph in FIG. 1 illustrates in full color a typical plant of 'DDTSS12-0' grown outdoors in Santa Paula, Calif. This plant is approximately 20 weeks old, shown in a 1 gallon pot.

Figure 2:
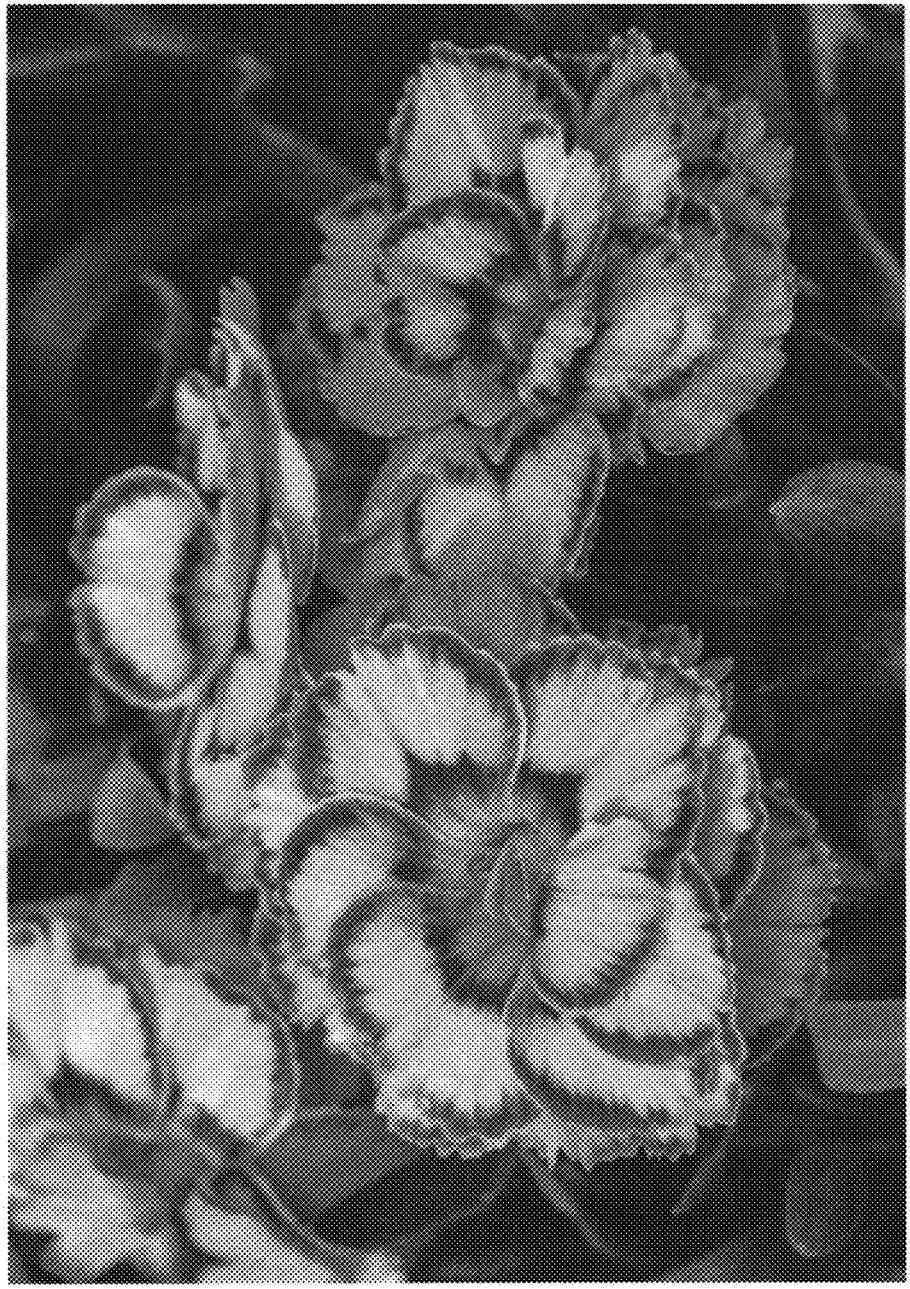

FIG. 2 illustrates a close-up view of the flowers.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Colour Chart, 2007, except where general terms of ordinary dictionary significance are used. The following observations and measurements describe 'DDTSS12-0' plants in a commercial greenhouse in Santa Paula, Calif. Temperatures ranged from 10° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Dianthus* hybrid 'DDTSS12-0'.

PROPAGATION

Time to initiate roots: About 10 days at approximately 24° C.

Time to produce a rooted cutting: About 18 days at 24 ° C.

Root description: Fibrous roots, approximately 1 to 3 mm in diameter, colored near Orange-White 159C.

PLANT

Pot size: 4 inches.

Plant type: Compact upright perennial.

Plant habit: Upright growing stems emerge basally.

Plant spread: Approximately 19 cm.

Height: Approximately 22 cm to top of flowering plane. Approximately 17 cm to top of foliar plane.

Length plant stem: Average 10 cm.

Diameter of plant stem: Approximately 3.0 mm.

Quantity stems: Approximately 30.

Stem:

*Color*.—Near Yellow-Green N138A.

*Texture*.—Smooth.

Internode length: Average 2.5 cm.

FOLIAGE

Leaf:

*Arrangement*.—Opposite (in pairs).

*Quantity*.—Approximately 10-12 fully expanded per stem. Average range of 4-6 immature leaves per stem.

*Average length*.—4.0-6.0 cm.

*Average width*.—0.5-1.0 cm.

*Shape of blade*.—Linear.

*Apex*.—Acute.

*Base*.—Clasping.

*Attachment*.—Sessile.

*Margin*.—Entire.

*Texture of top surface*.—Smooth.

*Texture of bottom surface*.—Smooth.

*Pubescence*.—None.

*Color*.—Young foliage upper side: Near Green N138A. Young foliage under side: Near Green N138A. Mature foliage upper side: Near Green N138B. Mature foliage under side: Near Green N138B.

*Venation*.—Type: Linear with a prominent mid vein. Venation color upper side: Indistinguishable from foliage. Venation color under side: Indistinguishable from foliage.

FLOWER

Natural flowering season: Perpetual flowering.

Inflorescence type and habit: Umbel of 1 to 3 double flowers.

Flower longevity on plant: 2-3 weeks.

Quantity of flowers: Approximately 40 flowers on a 20 week old plant.

Persistent or self-cleaning: Persistent.

Fragrance: Moderately strong floral scent.

Inflorescence size:

*Diameter*.—Approximately 6.0 cm.

*Height*.—Approximately 3.5 cm.

Individual flower size:

*Diameter*.—Approximately 3.5 cm.

*Length*.—Approximately 3.0 cm.

Petals:

*Petal arrangement*.—Whorled, multiple whorl.

*Shape*.—Spatulate, with an elongated narrow base and orbicular distal section.

*Base*.—Attenuate.

*Margin*.—Serrated.

*Apex*.—Sharply serrated or notched.

*Length*.—2.0-2.5 cm.

*Width*.—Approximately 1.5 cm.

*Petal quantity*.—Average range 16 to 20.

*Texture*.—Smooth all surfaces.

*Aspect*.—Flat to slightly undulating.

Color:

*When opening*.—Upper surface: Near Red-Purple 63D, with Red-Purple 61A flare toward base, and scattered around outer edge. Base near Red-Purple 63D. Lower surface: Near Red-Purple 63D.

*Fully opened*.—Upper surface: Near Red-Purple 62C, with Red-Purple 61A flare toward base, and scattered around outer edge. Base near Red-Purple 63D. Lower surface: Near Red-Purple 62C.

*Fading*.—Upper surface: Near Red-Purple 62C, with Red-Purple 61A flare toward base, and scattered around outer edge. Base near Red-Purple 63D. Lower surface: Near Red-Purple 62C. Base near Red-Purple 63D.

Tube:

*General description*.—Tube consists of the elongated, unfused base of the petals. Tube shape caused by a fused calyx.

*Length*.—2.0 cm.

*Width*.—0.5 cm.

*Texture*.—Smooth.

Color:

*Fully opened*.—Inner surface: Near Green 138B. Outer surface: Near Green 138B.

Bud:

*Shape*.—Elongated cylinder.

*Length*.—Average 1.0 cm.

*Diameter*.—Average 0.5 cm.

*Color*.—Near Green 138C.

Sepals:

*Quantity*.—4.

*Arrangement*.—Fused tube.

*Shape*.—Cylindric.
*Length*.—1.0 cm.
*Width*.—4.0 mm.
*Margin*.—Entire.
*Apex*.—Acute.
*Texture*.—Smooth upper and lower surfaces.
*Color*.—Near Green 138B.

Bracteoles:
*Shape*.—Strap shaped.
*Quantity per flower*.—2.
*Length*.—Approximately 1.0 cm.
*Width*.—Approximately 2 mm.
*Margin*.—Entire.
*Texture*.—Smooth.
*Color*.—Near Green N138A.

Peduncle:
*Length*.—1.0-2.0 cm.
*Diameter*.—2.0 mm.
*Color*.—Near Green N138A.
*Orientation*.—Upright.
*Strength*.—Flexible.
*Texture*.—Smooth.

Pedicel:
*Length*.—Average 0.5-1.0 cm.
*Diameter*.—1 mm.
*Color*.—Near Green N138A.
*Orientation*.—Upright.
*Strength*.—Flexible, elastic.

REPRODUCTIVE ORGANS

Stamens:
*Number*.—Most commonly 6.
*Filament length*.—Approximately 1 cm.

Anthers:
*Shape*.—Oblong.
*Length*.—Approximately 0.2 cm.
*Color*.—Near Greyed-Yellow 160C.
*Pollen*.—Not observed.

Pistil:
*Number*.—2.
*Length*.—Approximately 1.2 cm.
*Style*.—Length: Approximately 1.0 cm. Color: Near White N155B.

Stigma:
*Shape*.—Linear, arching.
*Color*.—White 155A.
*Ovary shape*.—Oblong.
*Ovary diameter*.—3 mm.
*Ovary length*.—6 mm.
*Ovary color*.—Near Green 139D.

OTHER CHARACTERISTICS

Seeds and fruits: Not observed to date.

Disease/pest resistance: Neither resistance nor susceptibility to the normal diseases and pests of *Dianthus* has been observed. Typical diseases of *Dianthus* include: *Alternaria dianthicola, Botrytis cinerea, Erwinia chrysanthemi, Pseudomonas caryophylli, Fusarium graminearum, Fusarium avenaceum, Fusarium culmorum* and *Rhizoctonia solani*, Typical pests include; various species of *Thysanopthera*, various *Aphis* species, and various species of *Tetranychus*.

Temperature tolerance: USDA zones 5 through 10 tolerant.

What is claimed is:

1. A new and distinct cultivar of *Dianthus* plant named 'DDTSS12-0' as herein illustrated and described.

* * * * *